United States Patent [19]

Kolar et al.

[11] Patent Number: 4,965,352
[45] Date of Patent: Oct. 23, 1990

[54] ANTHRACYCLINE DERIVATIVES HAVING CYTOSTATIC ACTIVITY

[75] Inventors: Cenek Kolar, Marburg; Michael Paal, Hamburg; Peter Hermentin; Hans P. Kraemer, both of Marburg, all of Fed. Rep. of Germany

[73] Assignee: Behringwerke Aktiengesellschaft, Marburg/Lahn, Fed. Rep. of Germany

[21] Appl. No.: 364,530

[22] Filed: Jun. 12, 1989

Related U.S. Application Data

[63] Continuation of Ser. No. 128,785, Dec. 4, 1987, abandoned.

[30] Foreign Application Priority Data

Dec. 8, 1986 [DE] Fed. Rep. of Germany ....... 3641835

[51] Int. Cl.$^5$ ............................................. G07H 15/00
[52] U.S. Cl. .................................... 536/6.4; 514/908; 514/883
[58] Field of Search .................. 536/6.4; 514/908, 883

[56] References Cited

U.S. PATENT DOCUMENTS

| | | | |
|---|---|---|---|
| 4,112,076 | 9/1978 | Arcamone et al. | 514/908 |
| 4,131,649 | 12/1978 | Penco et al. | 514/908 |
| 4,133,877 | 1/1979 | Masi et al. | 514/908 |
| 4,146,616 | 3/1979 | Penco et al. | 514/908 |
| 4,191,755 | 3/1980 | Masi et al. | 514/908 |
| 4,191,756 | 3/1980 | Masi et al. | 514/908 |
| 4,263,428 | 4/1981 | Apple et al. | 536/6.4 |
| 4,316,011 | 2/1982 | Oki et al. | 536/6.4 |
| 4,562,177 | 12/1985 | Horton et al. | 536/6.4 |
| 4,863,739 | 9/1989 | Perez-Soler et al. | 514/908 |

OTHER PUBLICATIONS

Essery et al., Can. J. Chem., vol. 58, 1980, pp. 1869–1874.

*Primary Examiner*—Ronald W. Griffin
*Assistant Examiner*—Everett White
*Attorney, Agent, or Firm*—Finnegan, Henderson, Farabow, Garrett and Dunner

[57] ABSTRACT

The invention relates to new anthracycline derivatives having cytostatic activity and the general formula I

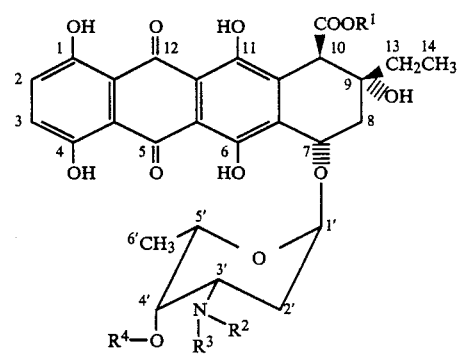

wherein
$R^1$ is a $CH_3(CH_2)_n$ group with n=0 to 3,
$R^2$ is a hydrogen atom or a methyl group,
$R^3$ is a hydrogen atom, a methyl group or an acyl protective group, and
$R^4$ is a hydrogen atom or an acyl protective group, and which are optionally in the form of a salt of an inorganic or organic acid, to a process for their preparation and to their use in pharmaceuticals.

31 Claims, No Drawings

ANTHRACYCLINE DERIVATIVES HAVING CYTOSTATIC ACTIVITY

This application is a continuation of application Ser. No. 07/128,785, filed Dec. 4, 1987, now abandoned.

The invention relates to new anthracycline derivatives having cytostatic activity, to a process for their preparation, and to their use in pharmaceuticals.

The anthracycline class of substances has been known for a long time now. Since the establishment of the structure of the rhodomycins, of adriamycin and of daunomycin, and the recognition of the cytostatic activity of certain representatives of the latter anthracycline class, a large number of anthracyclines has been obtained by biological means from representatives of the Actinomycetes genus Streptomyces, and their action has been investigated.

It is known that anthracyclines in which a daunosaminl or rhodosaminyl unit occurs have an antitumor action and that, for example, adriamycin and aclacinomycin are present as active substances in commercially available products.

A publication of Essery and Doyle (Can. J. Chem. 58, 869 (1980)), discloses the linkage between a functionalize daunosamine and a $\epsilon$-rhodomycinone. The resulting $\alpha$-glycoside has, however, only a weak cytostatic activity compared with adriamycin.

The extensive investigations carried out by the applicant have shown, surprisingly, that $\epsilon$-isorhodomycinone can undergo glycosidation with 1,4-di-O-acetyl-L-rhodosamine, and that the 7-O-$\alpha$-L-rhodosaminyl-$\epsilon$-isorhodomycnone which is formed thereby, and its 4'-O-acetyl derivati e, have cytostatic activity which is comparable with that of adriamycin.

Thus, the object of the present invention was to provide, starting from $\epsilon$-isorhodomycinone which is obtainable by biological means, or its derivatives appropriately substituted in the 10-position, new anthracycline derivatives which are distinguished by cytostatic activity.

In this connection, the new anthracycline derivatives according to the invention correspond to the general formula I

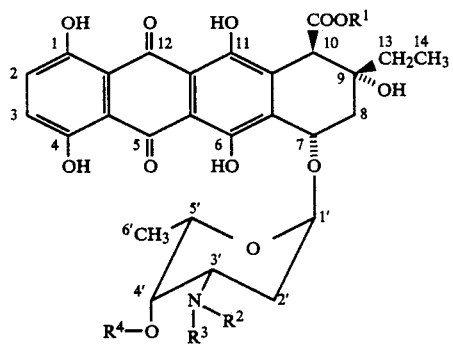

wherein
$R^1$ is a $CH_3(CH_2)_n$ group with n=0 to 3,
$R^2$ is a hydrogen atom or a methyl group,
$R^3$ is a hydrogen atom, a methyl group, or an acyl protective group which is customary in carbohydrate chemistry, such as an acetyl, trifluoroacetyl, benzoyl or para-nitrobenzoyl group,
$R^4$ is a hydrogen atom or an acyl protective group, and which are, where appropriate, in the form of a salt of an inorganic or organic acid which, of course, is tolerated from the health point of view.

Particularly preferred within the scope of the present invention are $\epsilon$-isorhodomycinone-glycosyl conjugates of the above mentioned general formula (I) wherein
$R^1$ is a methyl group,
$R^2$ is a hydrogen atom or a methyl group,
$R^3$ is a hydrogen atom or a methyl group, a trifluoroacetyl or acetyl group, and
$R^4$ is a hydrogen atom, an acetyl, benzoyl or para-nitrobenzoyl group, and which once again may, where appropriate, be in the form of a salt of an organic or inorganic acid.

The process according to the invention for the preparation of the new anthracycline derivatives described above starts from anthracyclinone, which can be obtained by biological means, or its derivative which is appropriately esterified in the 10-position, of the general formula II

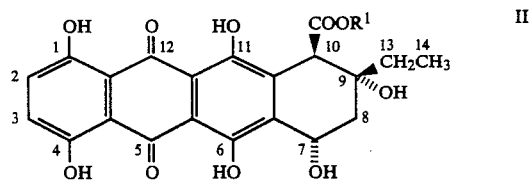

in which $R^1$ is a $CH_3(CH_2)_n$ group with n equal to 0 to 3. This anthracyclinone derivative is (a) reacted with a functionalized daunosamine derivative of the general formula III

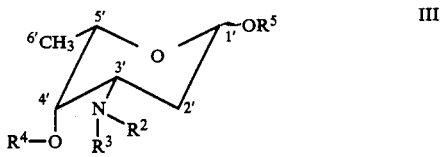

in which $R^2$ denotes a hydrogen atom or a methyl group, $R^3$ denotes a methyl group or an acyl protective group, $R^4$ denotes a protective group, and $R^5$ denotes an acyl protective group, in the presence of an organic solvent, of a catalyst and, where appropriate, of an acid binding substance and a desiccant, at a reaction temperature of $-70°$ C. to $+30°$ C., to give a compound of the general formula (I), there being, where appropriate, (b) partial or complete removal in a manner known per se, using an inorganic or organic base in a solvent, of the protective groups on the carbohydrate segment in a reaction product from stage (a), and, where appropriate, selective reintroduction of a new acyl protective group on the 4'-hydroxy and/or 3'-amino group or 3'-methylamino group and, where appropriate, (c) elimination, in a manner known per s by photolytic means in the presence of a solvent at a reaction temperature of $+10°$ C. to $+100°$ C., of a methyl group bonded to nitrogen in a 3'-N,N-dimethylamino reaction product obtained in stage (a) or (b), and, where appropriate, conversion of the 3'-N-methylamino derivitive which is formed into a N-acyl derivative or a N-acyl, O-acyl derivative, and, where appropriate, (d) carrying out, in a manner known per se, on a daunosamine react on product obtained in stage (b) a N-methylation to give the 3-N-methyldaunosamine reaction product, or a N,N-dimethylation to give the rhodosamine reaction product, and, where appropriate, (e) conversion, in a manner known per se, of a product from stage (a), (b), (c) or (d) into the salt of an inorganic acid or organic acid.

Examples of protective groups which can be carried by the daunosamine derivative used in the process according to the invention are as $R^3$ an acyl protective group customary in carbohydrate chemistry, such as an acetyl or trifluoroacetyl group, as $R^4$ a blocking acetyl, benzoyl or para-nitrobenzoyl group customary in carbohydrate chemistry, and as $R^5$ an acetyl or para-nitrobenzoyl group.

Examples of organic solvents in which the reaction can be carried out are chloroform, dichloromethane, toluene, ether, dimethylformamide, acetone, acetonitrile, or mixtures thereof, and an example of a catalyst which can be used is trimethylsilyl trifluoromethanesulfonate. It is expedient to use acid binding substance 4 molecular sieves and as desiccant calcium sulfate, for example.

The cleavage of the protective groups in stage (b) can be carried out using a base, such as alkali or alkaline-earth metal hydroxides, sodium carbonate and triethylamine, in a solvent such as water, methanol, ethanol, THF or mixtures thereof.

The photolytic elimination of a methyl group carried out in stage (c) can be brought about by the action of a light source such as, for example, sunlight or daylight, or of a strong light emitter, examples of suitable solvent being chloroform, methanol, water or mixtures thereof.

It is inherently possible to use any desired methylating agent for the methylation of the 3'-amino group provided for in stage (d). An example which may be mentioned for the formation of the N,N-dimethyl compound is methylation with 37% strength aqueous formaldehyde and sodium cyanoborohydride.

It is inherently possible to use any desired inorganic or organic acid for the salt formation in stage (e) of the process, as long as, in view of the subsequent use in pharmaceuticals, the acid is tolerated from the health point of view. Glutamic acid or glucuronic acid is preferably used.

According to a preferred embodiment of the process according to the invention, ε-isorhodomycinone is reacted with 1,4-di-O-acetyl--L-rhodosamine in the presence of an organic solvent, of a catalyst and. where appropriate of an acid binding substance and a desiccant and the product is subjected to photolytic elimination of a methyl group where appropriate, to deacylation, and to renewed acylation and salt-formation where appropriate.

According to another advantageous embodiment of the process according to the invention, ε-isorhodomycinone is reacted with 1,4-di-O-acetyl-3-N-acetyl-α-L-daunosamine in the presence of an organic solvent of a catalyst and, where appropriate, of an acid binding substance and a desiccant, and the product is subjected to, where appropriate, deacylation and N-methylation and, where appropriate, renewed acylation and/or salt-formation.

The new anthracycline derivatives obtained by the process according to the invention are, as already mentioned, distinguished by cytostatic activity, and hence they can be processed, together with the customary pharmaceutical manufacturing aids and/or diluents, to give pharmaceuticals for use in cancer therapy. In this connection, the methods of dosage and use essentially correspond to those for the known substances adriamycin, daunomycin, aclacinomycin, 4'-epi-adriamycin, 4'-methoxyadriamycin or 4'-deoxyadriamycin.

The pharmaceuticals prepared in this way can additionally contain other active substances as long as the latter do not show undesired side effects with the compounds according to the invention.

The cytostatic activity of the compounds according to the invention has been tested using mouse L1210 leukemia cells. Use was made for this of the formation of L1210 leukemia cell colonies in soft agar. This method is used to detect the effect of the test substances on the growth behavior of the cells over several generations. In this connection, with a cell cycle time of 10 to 12 hours, about 14 consecutive generations are observed in the 7-day duration of the test. In this test, the substances having cytostatic activity according to the invention bring about a reduction, compared with an untreated control sample, in the number of colonies which is to be observed.

Details of the test method are evident from the procedure for determining the formation of colonies given herein after. Appropriate tests on NMRI mice were carried out to determine the acute toxicity of the anthracycline derivatives according to the invention. Details of the test method are evident from the procedure for determining the acute toxicity given hereinafter.

Procedure for the formation of L1210 leukemia cell colonies in soft agar 500 leukemia cells per plate were incubated with various concentrations of the test substance at 37° C. for 1 hour. The cells were then washed twice with McCoy 5A medium, 0.3% agar was added, and finally the mixture was poured into Petri dishes. Controls were incubated only with fresh medium. In place of the incubation for one hour, in some cases various concentrations and test substances were mixed with the upper agar layer in order in this way to achieve continuous exposure of the cells throughout the incubation time. After the agar had solidified, the plates were incubated in an incubator at 37° C. for 7 days (5% by volume $CO_2$, 95% relative atmospheric humidity). Thereafter the number of colonies with a diameter of more than 60μ which had formed was counted. The results have been stated as the number of colonies in treated agar plates as a percentage of the untreated control. The dose-effect graph obtained in this way was used to determine the $IC_{50}$ as a measure of the activity of the substance. The results for the compounds described here are compiled in Table 1, comparing with adriamycin.

Procedure for determining the acute toxicity

Determination of the acute toxicity entailed intravenous injection of various doses of the test substance, disolved in 0.5 ml of physiological saline solution, in NMRI mice on day 0. Control groups received only 0.5 ml of physiological saline solution. 5 mice were used for each concentration of the test substance. The number of surviving mice was determined on day 14, and the $LD_{50}$ was determined therefrom by the Litchfield-Wilcoxon method. The toxicity of the compounds described here is compiled in Table 1, comparing with adriamycin.

| Compound | Cytotoxicity (continuous incubation) IC$_{50}$ (ug/ml) | Acute toxicity LD$_{50}$ (mg/kg) |
|---|---|---|
| 7-0-(4'-O-Acetyl-α-L-rhodosaminyl)-ε-isorhodomycinone | 0.028 | 89.0 |
| 7-O-(α-L-Rhodosainyl)-ε-isorhodomycinone | 0.035 | 50–100 |
| 7-O-(3'-N-Trifluoroacetyl-α-L-daunosaminyl)-ε-isorhodomycinone | 0.4 | — |
| 7-O-(4'-O-Acetyl-3'-N-methyl-α-L-daunosaminyl)-ε- isorhodomycinone | 0.1 | — |
| 7-O-(3'-N-Methyl-α-L-daunosaminyl)-ε-isorhodomycinone | 0.028 | — |
| Adriamycin | 0.02 | 26.5 |

The preparation process according to the invention is illustrated by Examples 1 to 11 which are detailed hereinafter and in which preferred compounds according to the invention have been prepared by the claimed process.

The structure of the prepared compounds was determined n using $^1$H and $^{13}$C NMR and MS or IR spectroscopy. The reactions were followed, and the resulting compounds were examined, by thin-layer chromatography or using HPLC techniques.

Example 1

7-O-(4'-O-acetyl--L-rhodosaminyl)-ε-isorhodomycinone (Compound 1)

1 g (2.25 mmol) of ε-isorhodomycinone was dissolved in 200 ml of anhydrous dichloromethane. 0.65 g (2.53 mmol) of 1,4-di-O-acetyl-L-rhodosamine and 5 g of 4 Å molecular sieves in 20 ml of anhydrous dichloromethane were added to this solution at room temperature, and the mixture was then stirred for 0.5 h. Thereafter, 0.6 ml of trimethylsilyl trifluoromethanesulfonate was added. After 0.5 h, saturated sodium bicarbonate solution was added to the mixture. The organic phase was washed with water, dried over sodium sulfate and concentrated in vacuo (water pump). Purification was by column chromatography on 80 g of silica gel (eluent: toluene/ethanol 10:1). 0.8 g 55% yield based on aglycone) of the title compound 1 was obtained.

Melting point: 223°–224° C.

Elemental analysis: Calculated (%): C 59.71; H 5.79; N 2.17; Found (%): C 59.97; H 5.81; N 2.03.

Spectroscopic data: $^1$H NMR (400 MHz, CDCl$_3$, δ): 5.68 (m, H-1'), 5.27 (dd, H-4'), 5.22 (dd, H-7), 4.49 (H-3'), 4.24 (H-10), 4.20 (H-5'), 3.70 (s, OCH$_3$), 2.19 (s, N(CH$_3$)$_2$), 2.18 (s, Ac).

Example 2

7-O-(α-L-rhodosaminyl)-ε-isorhodomycinone (Compound 2)

0.5 g (0.77 mmol) of compound 1 was dissolved in 100 ml of anhydrous methanol, and 0.1 ml of 30% strength sodium methylate solution was added. After stirring at room temperature for 2 h, the mixture was neutralized with Dowex WX8 ion exchange resin. It was then filtered, and the filtrate was concentrated in vacuo. 0.35 g (90%) of the title compound 2 was obtained.

Elemental analysis: Calculated (%): C 59.89; H 5.86;N 2.32;

Found (%): C 59.97; H 5.91; N 2.13;

Spectroscopic data: $^1$HNMR (400 MHz, CDCl$_3$, δ): 5.52 (dd, H-1'), 5.23 (H-7), 4.50 (H-9), 4.27 (H-10), 4.07 (H-5'), 3.73 (OCH$_3$), 2.25 (N(CH$_3$)$_2$).

Example 3

7-O-(4'-O-para-nitrobenzoyl-3-N-trifluoroacetyl-α-L-daunosaminyl)-ε-isorhodomycinone (Compound 3)

1.0 g (2.25 mmol) of ε-isorhodomycinone was dissolved in 200 ml of anhydrous dichloromethane/ether 1:1, and 5 g of 4 Å molecular sieves were added, and the mixture was stirred at room temperature for 30 min. The suspension was cooled to −20° C. and then 3.25 g (6 mmol) of 1,4-di-0-para-nitrobenzoyl-3-N-trifluoroacetyl-L-daunosamine dissolved in 50 ml of dichloromethane were added. 1 ml of trimethylsilyl trifluoromethanesulfonate was then added wise. After 30 minutes, 2.2 ml of trimethylamine were added to the reaction mixture, which was then stirred for 10 minutes more. The reaction mixture was filtered, and the residue on the filter was washed with dichloromethane. The organic solutions were washed with water and dried over anhydrous sodium sulfate. The residue obtained by evaporation of the solvent was chromatographed on silica gel. 1.52 g (yield 82% based on aglycone) of compound 3 were obtained.

Elemental analysis: Calculated (%): C 54.28; H 4.06; N 3.42; F 6 69; Found (%): C 54.02; H 4.06; N 3.28;F 6 80.

Example 4

7-O-(4'-O-acetyl-3'-N-trifluoroacetyl-α-L-daunosaminyl)-ε-isorhodomycinone (Compound 4)

Starting from ε-isorhodomycinone and 1,4-di-O-acetyl-3-N-trifluoroacetyl-L-daunosamine, the compound 4 was prepared as described in the procedure for the preparation of compound 3, but in this case the reaction solvent use was a 1:1 dichloromethane/acetone solvent mixture.

Melting point: 238° C.

Elemental analysis: Calculated (%); C 54.01; H 4.53; N 1.96; Found (%); C 54.03; H 4.61; N 1.79.

Spectroscopic data: $^1$H NMR (400 MHz, CDCl$_3$, δ): 5.49 (dd, H-1'), 5.32 (d, J=7.0 Hz, NHCO), 5.20 (dd, H-4'), 5.12 (H-7), 4.33 (m, H-5' and H-3'), 4.27 (s, H-10), 3.68 (s, OCH$_3$).

Example 5

7-O-(3'-N-trifluoroacetyl-α-L-daunosaminyl)-ε-isorhodomycinone (Compound 5)

200 mg (0.24 mmol) of compound 3 were dissolved in 20 ml of methanol and, at room temperature, 0.1 ml of aqueous 0.1N NaOH solution was added. After 10 minutes, the reaction mixture was neutralized with 0.1 ml of aqueous 0.1N HCl solution. The product obtained after evaporation of the solvent was then purified on a short silica gel column. Yield of title compound 5: 149 mg (93%).

Elemental analysis: Calculated (%); C 53.81; H 4.51; N 2.09; F 8.51; Found (%): C 54.01; H 4.52; N 2.03; F 8.38.

EXAMPLE 6

7-O-α-L-daunosaminyl-ε-isorhodomycinone (Compound 6)

Compound 5 was deblocked to give compound 6 in accordance with the procedure described in Example 5, but using 0.5N NaOH.

Melting point: 153°–155° C.

Elemental analysis: Calculated (%); C 58.64; H 5.45; N 2.44; Found (%); C 58.37; H 5.51; N 2.32.

Spectroscopic data: $^1$H NMR (270 MHz, CD$_3$OD, δ): 7.18 (H-2, H-3), 5.47 (H-1'), 5.11 (H-7), 4.2 (H-10), 3.73 (COOCH$_3$).

IR: (KBr, ν, cm$^{-1}$): 1,720, 1,590

EXAMPLE 7

7-O-(3'-N-acetyl-4'-O-acetyl-α-L-daunosaminyl)-ε-isorhodomycinone (Compound 7)

Compound 6 was converted by the acetylation method customary in carbohydrate chemistry, using acetic anhydride/pyridine/dichloromethane into the 3'-N, 4'-O-diacetyl derivative.

Spectroscopic data: $^1$H NMR (400 MHz, CDCl$_3$, δ) 5.49 (H-1'), 5.32 (J(NH, 3')=7 Hz, NHCO), 5.20 (H-4'), 5.12 (H-7), 4. 3 (m, H-5', H-3'), 4.27 (s, 10-H), 3.68 (OCH$_3$), 2.19 (OAc), 2.17 (NAc).

EXAMPLE 8

7-O-(4'-O-acetyl-3'-N-methyl-α-L-daunosaminyl)-ε-isorhodomycinone (Compound 8).

A solution of 7-O-(4'-O-acetyl-L-rhodosaminyl)-ε-isorhodomycinone (compound 1) (50 mg =0.078 mmol) in a mixture of chloroform (100 ml) and methanol (5 ml) in a Petri dish of diameter of 19 cm was exposed at 0° C., on a reflecting underlay, for 1 hour to a 500 watt lamp (Schiansky) at a distance of about 25 cm. The solvent was then removed in a rotary evaporator, the residue was dissolved in the minimum of methanol. Water was added, the pH was adjusted to 4.4 with 1% strength hydrochloric acid, and the methanol was removed in a rotary evaporator. The remaining aqueous solution was extracted three times with chloroform. The combined chloroform phases were back-extracted three times with water of pH 4.5 and then once with water of pH 9.5, and were dried over sodium sulfate and filtered, and the solvent was removed in a rotary evaporator. The residue was purified by repeated dissolving in dichloromethane and precipitation by addition of hexane, and thin-layer chromatography was used for detection.

Yield of the title compound 8: 26 mg (0.041 mmol)=53%

Spectroscopic data: $^1$H NMR (400 MHz, CDCl$_3$): 1.13 (t, 3H, J=7.3 Hz, CH$_3$-14), 1.20 (d, 3H, J$_{5,6'}$=6.5 Hz, CH$_3$-6'), 2.18 (s, 3H, acetyl-CH$_3$), 2.33 (s, 3H, N-CH$_3$), 2.83 (bd, 1H, J$_{3',2'a}$=11.7 Hz, H-3'), 3.71 (s, 3H, COOCH$_3$) 4.21 (q, 1H, J$_{5',6'}$=6.5 Hz, H-5'), 4.29 (s, 1H, H-10), 4.38 (s, 1H, OH-9) 5.18 (s, 1H, H-4'), 5.25 (d, 1H, J$_{7,8}$=2.2 Hz, H-7), 5.52 (d, 1H, J$_{1',2'}$=3.4 Hz, H-1'), 7.29 (s, 2H, H-2 and H-3).

EXAMPLE 9

7-O-(3'-N-methyl--L-daunosaminyl)-ε-isorhodomycinone (Compound 9)

A solution of 7-O-α-L-rhodosaminyl-ε-isorhodomycinone (compound 2) (62 mg=0.103 mmol) in a chloroform/methanol mixture (20/1) (310 ml) was demethylated by photolysis in analogy to Example 8, the reaction being followed by thin-layer chromatography. Once the starting compound had been consumed, the solvent was removed in a rotary evaporator, and the reaction product was subjected to repeated column chromatography (10 g of silica gel 60 for HPLC, 25–40 μm, Merck; mobile phase: dichloromethane/methanol/water (80/8/1)). Residues of silica gel were removed by extracting the purified solid product several times with chloroform and recovering it from the combined chloroform phases.

Yield of title compound 9: 27 mg (not optimized)

Spectroscopic data: $^1$H NMR (270 MHz, CDCl$_3$): 1.13 (t, 3H, J=7.3 Hz, CH$_3$-14), 1.37 (d, 3H, J$_{5',6'}$=6.5 Hz, CH$_3$-6'), 2.39 (bs, 3H, N-CH$_3$), 2.81 (bd, 1H, J$_{2',3'}$ about 10 Hz, H-3'), 3.72 (s, 3H, COOCH$_3$), 4.10 (q, J$_{5',6'}$=6.5 Hz, H-5'), 4.28(s, 1H, H-10), 4.43 (bs, 1H, OH-9), 5.25 (d, 1H, J$_{7,8}$=2.0 Hz, H-7), 5.49 (d, 1H, J$_{1',2'}$=2.5 Hz, H-1'), 7.30 (s, 2H, H-2 and H-3).

The molecular peak in the mass spectrum M+H$^⊕$=588) is consistent with the calculated molecular mass of 587.6 (C$_{29}$H$_{33}$NO$_{12}$).

EXAMPLE 10

7-O-(3'-N-acetyl-3'-N-methyl-α-L-daunosaminyl)-ε-isorhodomycinone (Compound 10)

A solution of 7-O-(4'-O-acetyl-3'-N-methyl-α-L-daunosaminyl)-ε-isorhodomycinone (15 mg=0.024 mmol) in dry methanol was isomerized in the presence of catalytic amounts of sodium methylate to the 3'-N-acetyl product, and the conversion was followed by thin-layer chromatic graphy. After the reaction was complete, the mixture .as neutralized with a strongly acidic Dowex 50 WX8 ion exchanger and was filtered, and the solvent was removed in a rotary evaporator.

Spectroscopic data: $^1$H NMR (400 MHz, CDCl$_3$): 1.13 (t, 3H, J=7.2 Hz, CH$_3$-14), 1.28 (d, 3H, J$_{5',6'}$=6.4 Hz, CH$_3$-6'), 1.47 (m, 1H, H-13 α), 1.84 (m, 1H, H-13 8β), 2.04 (s, 3H, N—CO—CH$_3$; 2.1–2.4 (m, CH$_2$-8), 2.99 (s, 3H, N-CH$_3$), 3.71 (s, 3H, COOCH$_3$), 3.81 (bs, 1H, H-4'), 4.17 (q, 1H. H-5'), 4.30 (s, 1H, H-10), 5.24 (bs, 1H, H-7), 5.55 (bs, 1H, H-1'), 7.31 (s, 2H, H-2 and H-3).

EXAMPLE 11

7-O-α-L-rhodosaminyl-ε-isorhodomycinone (Compound 2)

30 mg (0.05 mmol) of compound 6 were dissolved in 10 ml of methanol. 0.1 ml of a 37% strength aqueous formaldehyde solution and 30 mg of sodium cyanoborohydride were added, and then the reaction mixture was stirred for 3 d. It was then evaporated to dryness, and the resulting residue was purified by chromatography on silica gel. 34 mg of compound 2 were obtained. HPLC investigation revealed that this compound was identical to the compound 2 described in Example 2.

We claim:

1. An anthracycline having cytostatic activity and the formula I:

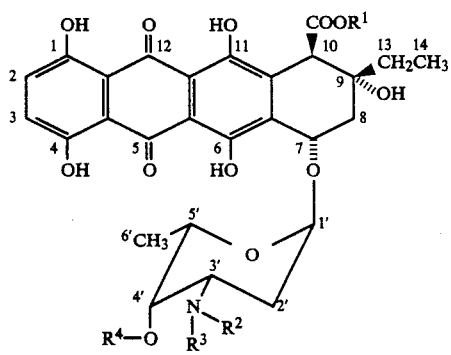

wherein $R^1$ is a $CH_3(CH_2)_n$ group in which n is 0 to 3, $R^2$ is a hydrogen atom or a methyl group, $R^3$ is a hydrogen atom, a methyl group or an acyl protective group, and $R^4$ is a hydrogen atom or an acyl protective group, or an inorganic or organic acid salt thereof.

2. An anthracycline as claimed in claim 1, wherein in formula I $R^1$ is a methyl group, $R^2$ is a hydrogen atom or a methyl group, $R^3$ is a hydrogen atom or a methyl, trifluoroacetyl or acetyl group, and $R^4$ is a hydrogen atom or an acetyl, benzoyl or paranitrobenzoyl group.

3. The compound 7-O-(4'-O-acetyl-α-L-rhodosaminyl)-ε-isorhodomycinone.

4. The compound 7-O-(α-L-rhodosaminyl)-ε-isorhodomycinone.

5. The compound 7-O-(3'-N-trifluoroacetyl-α-L-daunosaminyl)-ε-isorhodomycinone.

6. The compound 7-O-(4'-O-acetyl-3'-N-methyl-α-L-daunosaminyl)-ε-isorhodomycinone.

7. The compound 7-O-(3'-N-methyl-α-L-daunosaminyl)-ε-isorhodomycinone.

8. A process for the preparation of an anthracycline as claimed in claim 1, which comprises a reacting step wherein an anthracyclinone of the formula II:

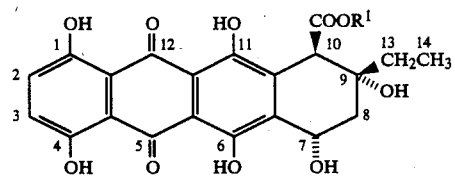

in which $R^1$ is a $CH_3(CH_2)_n$ group and n is 0 to 3, is reacted with a functionalized daunosamine of the formula III:

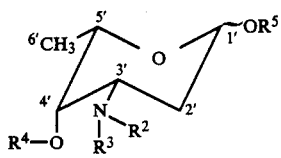

in which $R^2$ is a hydrogen atom or a methyl group, $R^3$ is a methyl group or an acyl protective group, $R^4$ is an acyl protective group, and $R^5$ is an acyl protective group, in the presence of an organic solvent and a catalyst to give a compound of the formula I.

9. The process as claimed in claim 8, which further comprises utilizing an acid binding substance and a desiccant, at a reaction temperature of about −70° C. to +30° C. in said reacting step.

10. The process as claimed in claim 8, which further comprises removing the protective groups on the carbohydrate segment of the product from said reacting step by use of an inorganic or organic base in a solvent.

11. The process as claimed in claim 10, which further comprises selectively reintroducing an acyl protective group on at least one of the 4'-hydroxy, 3'-amino or 3'-methylamino groups of said product.

12. The process as claimed in claim 10, which further comprises eliminating, by photolytic means in the presence of a solvent at a reaction temperature of about 10° C. to about 100° C., a methyl group bonded to nitrogen in a 3'-N, N-dimethylamino reaction product of said reacting step.

13. The process as claimed in claim 12, which further comprises converting the 3'-N-methylamino derivative thus formed into an N-acyl or an N-acyl, O-acyl derivative.

14. The process as claimed in claim 10, which further comprises N-methylating a daunosamine product obtained in claim 14 to give 3-N-methyldaunosamine or N,N-dimethylating a daunosamine product obtained in claim 10 to give a rhodosamine product.

15. The process as claimed in claim 8, which further comprises eliminating, by photolytic means in the presence of a solvent at a reaction temperature of about 10° C. to about 100° C., a methyl group bonded to nitrogen in a 3'-N,N-dimethylamine reaction product of said reacting step.

16. The process as claimed in claim 15 which further comprises converting the 3'-methylamino derivative thus formed into an N-acyl or an N-acyl, O-acyl derivative.

17. The process as claimed in claim 8, which further comprises converting the compound obtained from said reacting step into a salt of an inorganic or organic acid.

18. The process as claimed in claim 8, wherein ε-isorhodomycinone is reacted with 1,4-di-O-acetyl-α-L-rhodosamine in the presence of an organic solvent and a catalyst.

19. The process as claimed in claim 18, which further comprises utilizing an acid binding substance and a dessicant.

20. The process as claimed in claim 19, which further comprises subjecting the obtained product to renewed acylation.

21. The process as claimed in claim 18, which further comprises subjecting the resultant product to photolytic elimination of a methyl group.

22. The process as claimed in claim 18, which further comprises subjecting the resultant product to deacylation.

23. The process of claim 18, which further comprises converting the compound obtained into a salt of an inorganic or organic acid.

24. The process as claimed in claim 8, wherein ε-isorhodomycinone is reacted with 1,4-di-O-acetyl-3-N-acetyl-α-L-daunosamine in the presence of an organic solvent and a catalyst.

25. The process as claimed in claim 24, which further comprises utilizing an acid binding substance and a dessicant.

26. The process as claimed in claim 24, which further comprises subjecting the resultant product to photolytic elimination of a methyl group.

27. The process as claimed in claim 24, which further comprises subjecting the resultant product to deacylation.

28. The process as claimed in claim 24, which further comprises subjecting the resultant product to renewed acylation.

29. The process as claimed in claim 24, which further comprises converting the resultant compound into a salt of an inorganic or organic acid.

30. A unit dosage pharmaceutical composition for treating cancer, which comprises an effective amount of an anthracycline of claim 1 or a pharmaceutically acceptable salt thereof effective for said treatment in combination with a pharmaceutically acceptable carrier.

31. A method of treating cancer in a host which comprises administering thereto an effective amount of an anthracycline of claim 1 or a salt thereof effective for said treatment.

* * * * *